(12) United States Patent
Hirasawa et al.

(10) Patent No.: US 8,589,379 B2
(45) Date of Patent: Nov. 19, 2013

(54) REPORT GENERATION SUPPORT SYSTEM

(75) Inventors: Yosuke Hirasawa, Nasushiobara (JP); Takashi Kondo, Nasushiobara (JP); Koichi Terai, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/204,976

(22) Filed: Aug. 8, 2011

(65) Prior Publication Data

US 2012/0041949 A1   Feb. 16, 2012

(30) Foreign Application Priority Data

Aug. 11, 2010   (JP) .................................. 2010-180048
Jul. 6, 2011     (JP) .................................. 2011-149642

(51) Int. Cl.
*G06F 17/30*   (2006.01)

(52) U.S. Cl.
USPC .................. 707/708; 705/2; 705/3; 704/235; 714/38.1; 345/440; 382/128; 382/132; 715/200; 715/206; 715/207; 715/208

(58) Field of Classification Search
USPC .......... 707/708; 705/2–3; 704/235; 714/38.1; 345/440; 382/128, 132; 715/200, 715/206–208
See application file for complete search history.

(56) References Cited

U.S. PATENT DOCUMENTS

| | | | | |
|---|---|---|---|---|
| 4,315,309 A | * | 2/1982 | Coli .................................. | 705/3 |
| 5,277,188 A | * | 1/1994 | Selker ........................... | 600/508 |
| 5,333,616 A | * | 8/1994 | Mills et al. ..................... | 600/508 |
| 5,334,030 A | * | 8/1994 | Brilliott .......................... | 439/75 |
| 5,338,210 A | * | 8/1994 | Beckham et al. ............. | 439/131 |
| 5,626,144 A | * | 5/1997 | Tacklind et al. .............. | 600/538 |
| 5,785,043 A | * | 7/1998 | Cyrus et al. ................... | 600/525 |
| 5,848,259 A | * | 12/1998 | Pelfrey .......................... | 345/440 |
| 7,536,644 B2 | | 5/2009 | Fowkes et al. | |
| 7,899,684 B2 | * | 3/2011 | Fukatsu et al. ................... | 705/2 |
| 7,996,381 B2 | * | 8/2011 | Uber et al. .................... | 707/708 |

(Continued)

FOREIGN PATENT DOCUMENTS

| | | |
|---|---|---|
| CN | 101645111 A | 2/2010 |
| JP | 2008-200139 | 9/2008 |
| JP | 2009-230304 | 10/2009 |

OTHER PUBLICATIONS

Chinese Office Action mailed Jul. 5, 2013, in Chinese Patent Application No. 201110222441.2.

*Primary Examiner* — Frantz Coby
(74) *Attorney, Agent, or Firm* — Oblon, Spivak, McClelland, Maier & Neustadt, L.L.P.

(57) ABSTRACT

The report generation support system according to the embodiment comprises an input history recording part, operation history recording part, selection part, extraction part, and a display controller. The input history recording part records findings input at the time of generating a medical report and, by linking with an input start time and/or finish time of the findings. The operation history recording part records, as an operation history, the type of operation conducted on an image at the time of generating a report and the time when the operation was conducted by linking with the operated image. The selection part selects at least a part of findings in a report. The extraction part extracts a focus image in the selected findings, based on an input start time and/or finish time of the findings corresponding to the selected location, and the contents of the operation history of the corresponding time.

6 Claims, 15 Drawing Sheets

(56) References Cited

U.S. PATENT DOCUMENTS

| | | | |
|---|---|---|---|
| 8,132,057 B2* | 3/2012 | Jann et al. | 714/38.1 |
| 8,295,576 B2* | 10/2012 | Gadodia et al. | 382/132 |
| 2003/0182164 A1* | 9/2003 | Shabot et al. | 705/3 |
| 2004/0146190 A1* | 7/2004 | Kasai | 382/128 |
| 2004/0243447 A1* | 12/2004 | Kamiyama et al. | 705/3 |
| 2005/0075905 A1* | 4/2005 | Bennett et al. | 705/2 |
| 2005/0131737 A1* | 6/2005 | Joseph et al. | 705/2 |
| 2005/0226405 A1* | 10/2005 | Fukatsu et al. | 380/1 |
| 2006/0265249 A1* | 11/2006 | Follis et al. | 705/3 |
| 2008/0262874 A1* | 10/2008 | Toshimitsu | 705/3 |
| 2009/0171225 A1* | 7/2009 | Gadodia et al. | 600/508 |
| 2010/0088095 A1* | 4/2010 | John | 704/235 |
| 2010/0114598 A1* | 5/2010 | Oez | 705/2 |
| 2010/0114609 A1* | 5/2010 | Duffy et al. | 705/3 |
| 2011/0270633 A1* | 11/2011 | Uber, III et al. | 705/3 |

* cited by examiner

| OPERATION TIME | | OPERATION CONTENT | OPERATION IMAGE |
|---|---|---|---|
| 2010/07/07 | 09:50:00 | OPEN | Pic1 |
| 2010/07/07 | 09:50:10 | OPEN | Pic2 |
| 2010/07/07 | 09:50:30 | COORDINATE SHIFT | Pic1 |
| 2010/07/07 | 09:51:10 | CLOSE | Pic1 |
| 2010/07/07 | 09:51:20 | GRADATION CHANGE | Pic2 |
| 2010/07/07 | 09:58:00 | OPEN | Pic3 |
| 2010/07/07 | 10:00:30 | ENLARGEMENT | Pic3 |
| 2010/07/07 | 10:02:10 | CLOSE | Pic2 |

| START TIME | FINISH TIME | LOCATION OF FINDING |
|---|---|---|
| (a) 2010/07/07 09:50:00 | 2010/07/07 09:59:00 | 51-60 |
| (b) 2010/07/07 10:00:00 | 2010/07/07 10:12:10 | 1-50 |
| (c) 2010/07/07 10:15:30 | 2010/07/07 10:30:30 | 61-100 |

REPORT GENERATION SUPPORT SYSTEM

CROSS-REFERENCE TO RELATED APPLICATION

This application is based upon and claims the benefit of priority from Japanese Patent Application No. 2010-180048, filed Aug. 11, 2010 and Japanese Patent Application No. 2011-149642, filed Jul. 6, 2011; the entire contents of which are incorporated herein by reference.

FIELD

The embodiment of the present invention relates to a report generation support system.

BACKGROUND

Images taken by a medical imaging apparatus such as an X-ray imaging apparatus, X-ray CT apparatus, MRI (Magnetic Resonance Imaging) diagnostic apparatus, etc. are archived in a medical image archive apparatus (server).

A radiologist uses an input means such as a mouse, etc., and gives instructions to display, on a medical observation apparatus (viewer), an arbitrary image from images archived in the medical image archive apparatus. The radiologist also generates a medical report by inputting findings with respect to the image in an input column displayed by the medical report generation apparatus.

Herein, in case of newly examining (hereinafter, sometimes referred to as "current examination") a patient who was examined in the past (hereinafter, sometimes referred to as "previous examination"), the radiologist sometimes states temporal changes from the previous examinations in the medical report of a current examination.

Then, the radiologist is required to confirm an image under focus in the previous examination (hereinafter, sometimes referred to as "focus image"), or compare the focus image and an image of the current examination.

In this case, the selection of a focus image, the image selection of the current examination to compare with the focus image, or a parallel display operation of the focus image and the image of the current examination, etc. with respect to a medical observation apparatus, are conducted by the radiologist himself/herself.

For example, in case of selecting a focus image, the radiologist reads medical reports of the previous examinations and causes to display, on a medical image observation apparatus, several images which may be considered to correspond to the findings. The radiologist also selects, as a focus image, an image that is considered to be closest to the findings among these images.

BRIEF DESCRIPTION OF THE DRAWINGS

FIG. 5 is diagram showing a process result of the image operation history recording process according to the first embodiment.

FIG. 8 is diagram showing a process result of the input history recording process according to the first embodiment.

DETAILED DESCRIPTION

The report generation support system according to embodiments comprises an input history recording part, an operation history recording part, a selection part, an extraction part, and a display controller. The input history recording part records, as input history, findings input at the time of generating a medical report by linking with at least one of an input start time and a finish time of the findings. The operation history recording part records, as operation history, the type of operation conducted with respect to an image operated at the time of generating a medical report and the time when the operation was conducted by linking with the operated image. The selection part selects at least part of the findings within a medical report based on instructions input from the input part. The extraction part extracts a focus image in the findings selected by the selection part, based on at least one of an input start time and a finish time of the findings corresponding to the selected location, as well as the contents of the operation history of the corresponding time. The display controller causes the display to display focus images.

(Entire Configuration of the Medical Information System)

Figure 1:
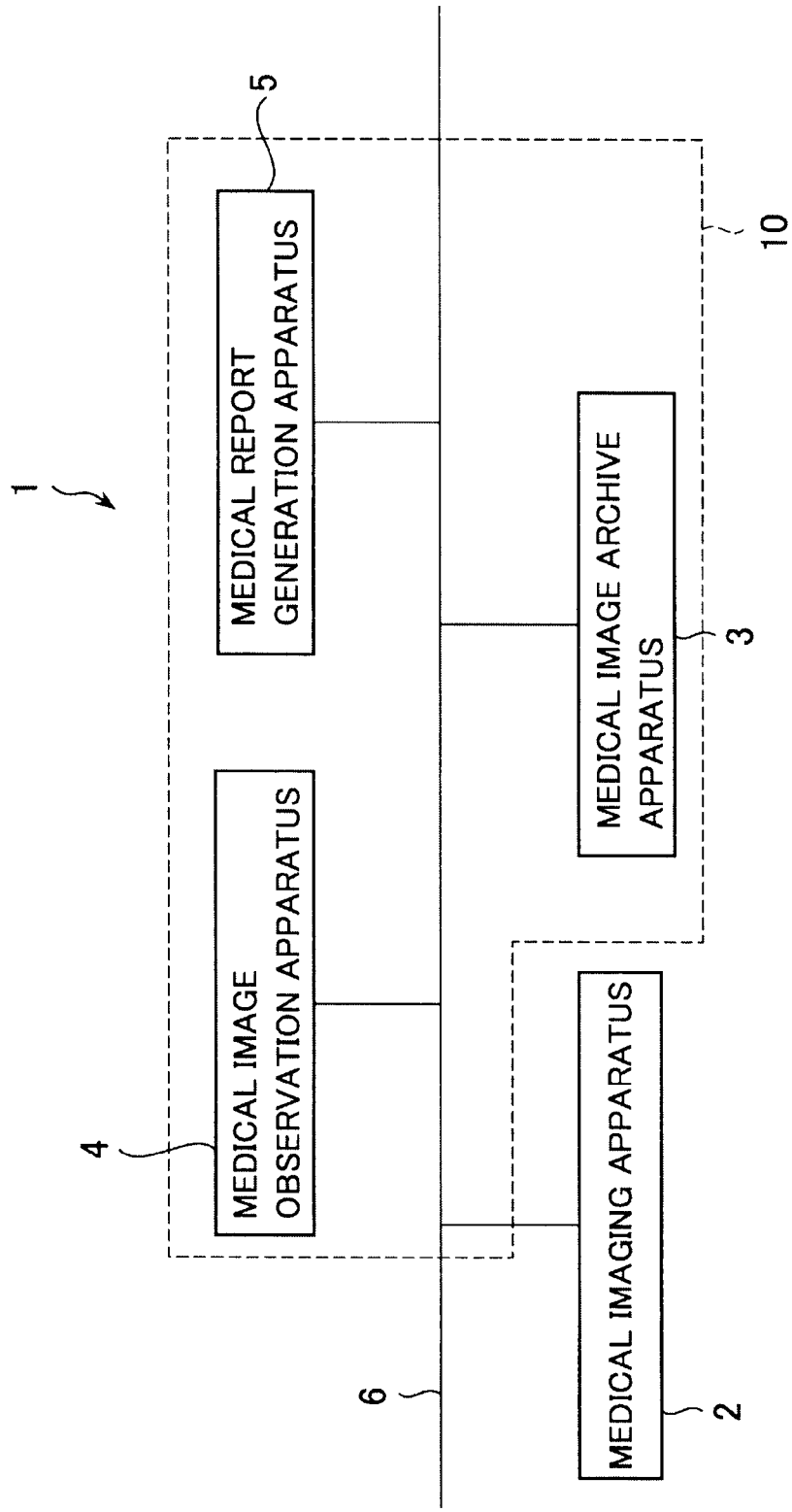
FIG. 1 is a general view of a medical information system that is common to embodiments.
Figure 2:
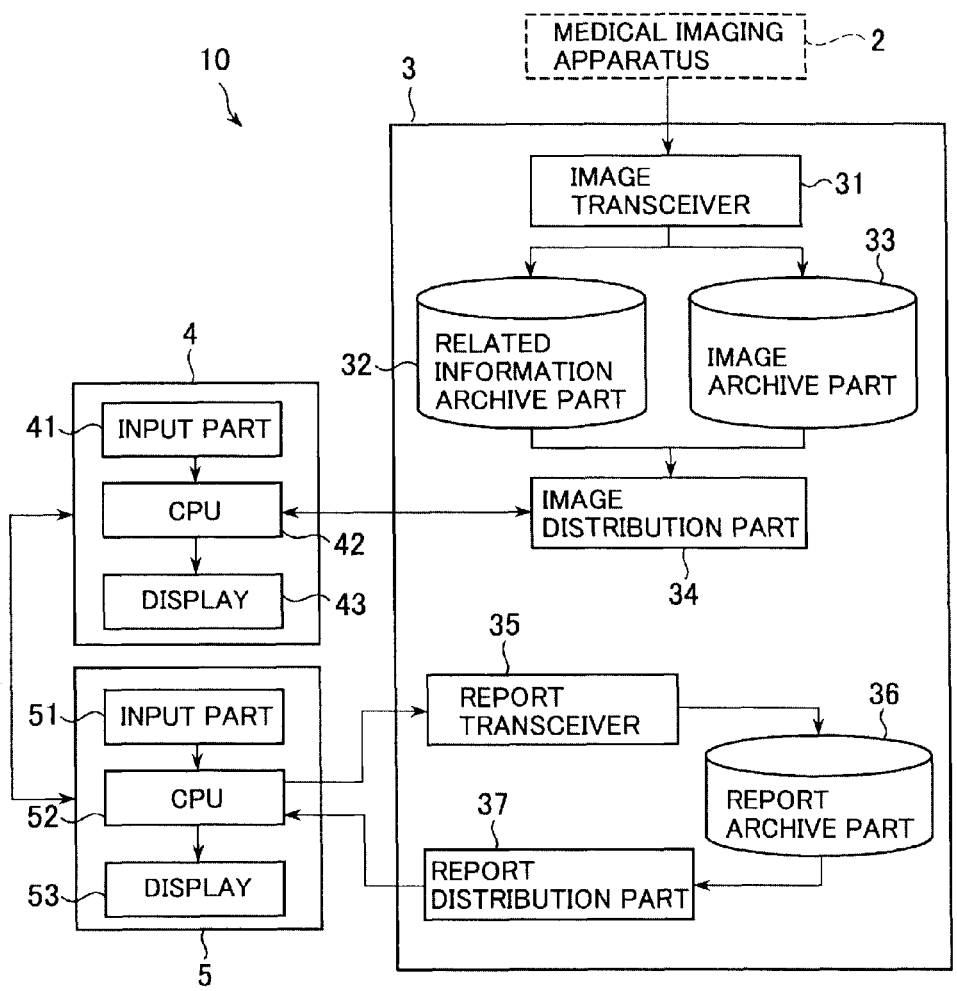
FIG. 2 is a general view of a report generation support system according to a first embodiment.

First, the entire configuration of the medical information system 1, including a report generation support system 10 in the present embodiment, is described using FIG. 1.

As shown in FIG. 1, the medical information system 1 comprises a medical imaging apparatus 2, a medical image archive apparatus 3 (hereinafter, sometimes referred to as "server part 3"), a medical image observation apparatus 4 (hereinafter, sometimes referred to as "viewer part 4"), and a medical report generation apparatus 5 (hereinafter, sometimes referred to as "report part 5"). Furthermore, these apparatuses are connected so as to be communicable via a LAN 6 (Local Area Network). In the present embodiment, the report generation part 5 itself, or the server part 3, the viewer part 4 and the report part 5 constitute the report generation support system 10. It should be noted that in the present embodiment, a configuration having a server part 3, a viewer part 4 and a report part 5 as separate bodies is described, but the server part 3, the viewer part 4, and the report part 5 may also be a single apparatus with each function.

The medical imaging apparatus 2 is an imaging apparatus such as an X-ray imaging apparatus, X-ray CT apparatus, MRI diagnostic apparatus, etc. By imaging a patient using these imaging apparatuses, medical images can be acquired. The acquired medical images are sent to the server part 3 in a file format complying with DICOM (Digital Imaging and Communications in Medicine). It should be noted that the medical images to be sent include image-related information associated with medical images such as the date when the medical image was taken.

The server part 3 is an apparatus for archiving medical images taken by the medical imaging apparatus 2, medical reports, etc.

The viewer part 4 is an apparatus for reading out a desired image among a plurality of medical images archived in the server part 3 so as to be displayed, based on instructions input by a radiologist, etc. The details of the viewer 4 are described later.

The report part 5 is an apparatus for generating medical reports with respect to medical images displayed in the viewer part 4 based on the instructions input from a radiologist, etc., by inputting findings in a findings input column. The details of the report part 5 are described later. It should be noted that the "findings" in the present embodiment are characters (a character string) composed of at least more than one character.

Embodiment 1

Embodiment 1 is described using FIG. 2 to FIG. 13.
(Configuration of the Report Generation Support System)
The configuration of the report generation support system 10 in the present embodiment is described in detail using FIG. 2. As described above, the report generation support system 10 in the present embodiment comprises the server part 3, the viewer part 4, and the report part 5.
(Configuration of the Server Part)

The server part 3 comprises an image transceiver 31, a related information archive part 32, an image archive part 33, an image distribution part 34, a report transceiver 35, a report archive part 36, and a report distribution part 37.

The image transceiver 31 functions to receive medical images sent from the medical imaging apparatus 2 (as well as associated medical image-related information) and send these medical images to the related information archive part 32 and the image archive part 33.

The related information archive part 32 functions to archive information related to the medical images sent from the image transceiver 32 (the date/time when the image was taken, imaging conditions, etc.).

The image archive part 33 functions to archive medical images sent from the image transceiver 31. It should be noted that the information related to medical images sent from the image transceiver 31 and medical images sent from the image transceiver 31 are mutually linked and archived.

The image distribution part 34 functions to distribute specific medical images along with the related information to the viewer part 4 based on instructions from the viewer part 4.

The report transceiver 35 functions to receive medical reports that have been sent from the report part 5 and send said medical reports to the report archive part 36.

The report archive part 36 functions to archive the medical reports sent from the report transceiver 35. It should be noted that related information for specifying a medical report such as patient ID, etc. is attached to the medical report.

The report distribution part 37 functions to distribute specific medical reports to the report part 5 based on instructions from the report part 5.
(Configuration of the Viewer Part)

The viewer part 4 comprises an input part 41, a CPU (Central Processing Unit) 42, and a display 43.

The input part 41 functions for a radiologist to conduct operation inputs with respect to the viewer part 4. The input part 41 is an operation input means such as a keyboard, mouse, etc.

Based on instructions input from the input part 41, the CPU 42 functions to read out corresponding programs from a ROM (Read Only Memory—not illustrated) or a RAM (Random Access Memory—not illustrated), and executes a prescribed process according to the program.

For example, when instructions are given by the input part 41 to display medical images related to one patient (specifically, an input of the patient ID), the CPU 42 executes a process for the medical image display based on a prescribed program. In this case, the CPU 42 first sends the patient ID to the server part 3 (image distribution part 34).

The image distribution part 34 reads out medical images corresponding to the patient ID (as well as associated image-related information) from the related information archive part 32 as well as the image archive part 33, and distributes the medical images to the display 43. The CPU 42 also executes a process of causing the display 43 to display the medical images.

The display 43 is a display means such as a monitor, etc. and functions to display medical images, etc. that have been processed by the CPU 42. Furthermore, medical images displayed in the display 43 may be subjected to a process of enlargement or reduction of medical images by an input operation at the input part 41. The CPU 42 controls the process based on a prescribed program.
(Configuration of the Report Part)

The report part 5 comprises an input part 51, a CPU 52, and a display 53.

The input part 51 comprises a function for a radiologist, etc. to conduct operation inputs with respect to the report part 5. The input part 51 is an operation input means such as a keyboard, mouse, etc. It should be noted that the input part 41 and the input part 51 are not required to be provided as a separate body, but may also be provided as an integrated input part.

Based on instructions input from the input part 51, the CPU 52 functions to read out a corresponding program from a ROM (Read Only Memory—not illustrated) or a RAM (Random Access Memory—not illustrated), and executes a prescribed process according to the program. It should be noted that the CPU 42 and the CPU 52 are not required to be provided as a separate body, but a CPU may also be integrally provided.

For example, when instructions for generating a medical report are given by the input part 51, the CPU 52 functions as a report generation part. That is, based on the input operation from the input part 51, a findings input column is displayed on the display 53 or a selection of the findings input column, and a process of inputting findings (a string of letters), etc. is executed.

Otherwise, based on instructions input from the input part 51, the CPU 52 is also capable of executing a process for acquiring specific medical reports from the server part 3. For example, when a patient ID is input by the input part 51, the CPU 52 sends the patient ID to the server part 3 (report distribution part 37). The report distribution part 37 reads out a medical report corresponding to the patient ID from the report archive part 36, and distributes said medical report to the report part 5. The CPU 52 conducts a process of causing the display 53 to display the medical report.

It should be noted that if there is a plurality of medical reports corresponding to the patient ID that has been input by the input part 51, the report distribution part 37 distributes all the medical reports to the report part 5. In this case, the CPU 52 conducts a process of causing the display 53 to display a table list of the plurality of medical reports (for example, by dates only). As a result of selecting a desired subject from the list by a radiologist, etc., the CPU 52 becomes capable of causing the display 53 to display the corresponding medical report.

The display 53 is a display means such as a monitor, etc. and functions to display medical reports. It should be noted that the display 43 and the display 53 are not required to be provided as a separate body, but may be provided as a single display.

(Regarding an Image Operation History Recording Process)

Figure 3:
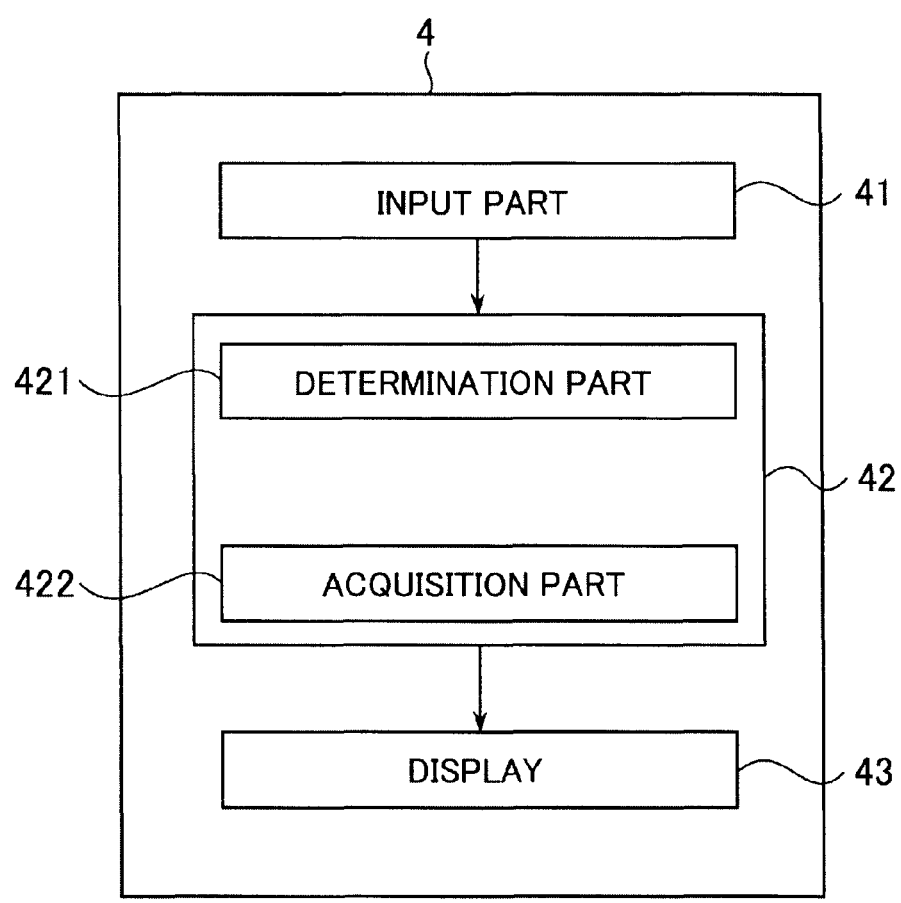
FIG. 3 is a diagram showing a configuration of a viewer part in an image operation history recording process according to the first embodiment.
Figure 4:
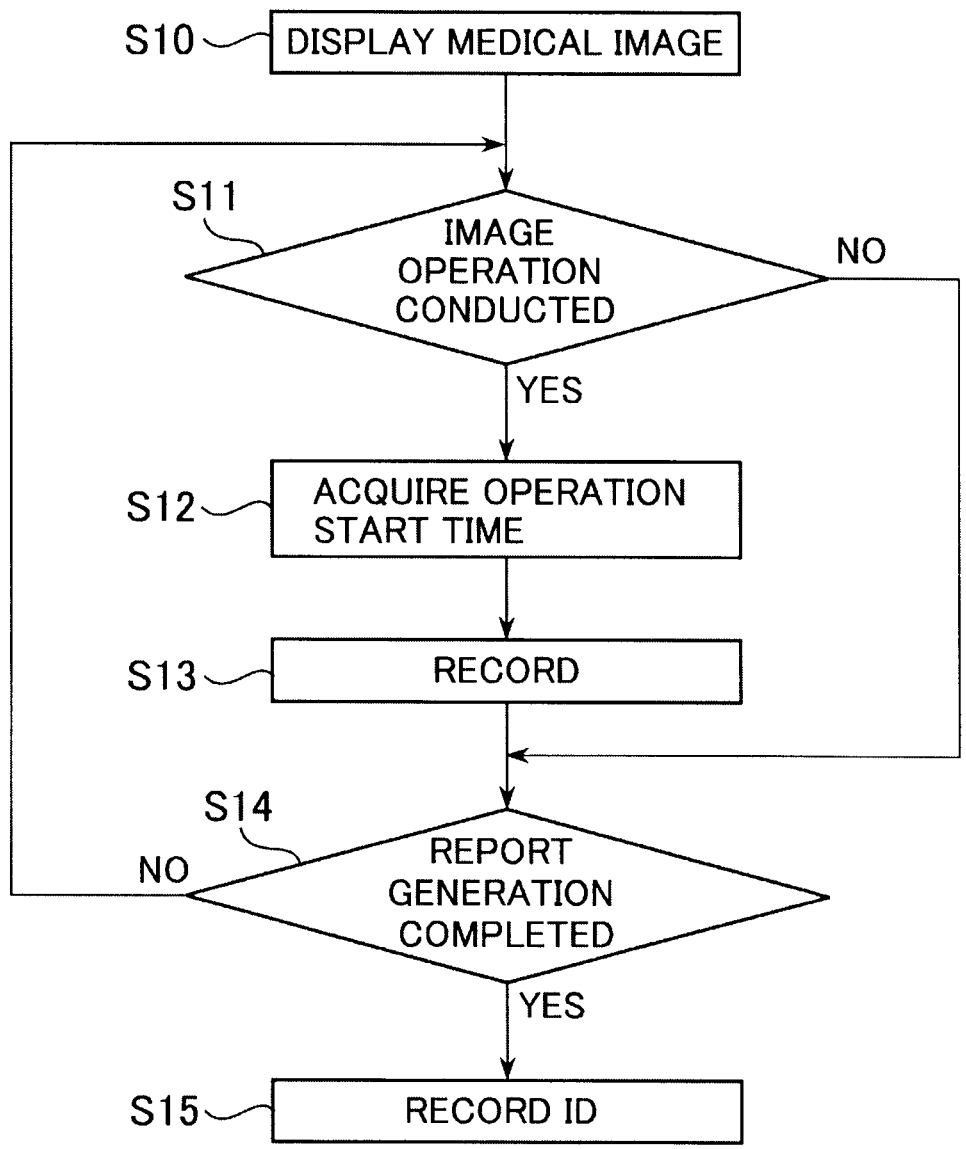
FIG. 4 is a flowchart of the image operation history recording process according to the first embodiment.

Next, an image operation history recording process in the present embodiment is described in detail using FIG. 3 to FIG. 5.

In the event of generating medical reports, a radiologist inputs findings in a findings input column while using medical images as references. In this event, sometimes a plurality of medical images is switched to be displayed or a specific medical image is subjected to enlargement or reduction operations, etc. In the present embodiment, a process of recording the history of operations conducted with respect to these medical images (hereinafter, sometimes referred to as "image operation history"), is conducted.

As shown in FIG. 3, the CPU 42 functions as a determination part 421 and an acquisition part 422 in an image operation history recording process.

The determination part 421 functions to determine whether or not an image operation was conducted with respect to the medical image displayed in the display 43 as well as the type of operation (enlargement, reduction, non-display, additional display, gradation change, measurement, annotation, etc.) when the image operation has been conducted. Specifically, when operation instructions to a medical image is input using the input part 41, the determination part 421 receives the input signal (image operation signal), making it possible to determine the start of the image operation as well as the type of operation. It should be noted that the determination part 421 sends the results of the determination to the acquisition part 422.

The acquisition part 422 functions to acquire the time when the operation was conducted on a medical image. Specifically, when an input signal from the determination part 421 is entered, the time corresponding to the input signal (time when the image operation started) is acquired.

Furthermore, in the present embodiment, the related information archive part 32 in the server part 3 functions to record the image operation history by linking with a medical image that has been operated. That is, the related information archive part 32 also functions as an "operation history recording part." It should be noted that it is also possible to provide a recording part within the viewer part 4 and record the image operation history as well as related medical images in the recording part.

FIG. 4 is a flow chart of an image operation history recording process.

Based on the instructions input from the input part 41, when a medical image is displayed in the display 43 (S10), first, the determination part 421 determines whether or not an image operation (the operation content, if an operation is being conducted) with respect to the medical image displayed on the display 43 is conducted (S11).

If an image operation is conducted (in case of Y in S11), the acquisition part 422 acquires the time when the operation with respect to the medical image has been conducted (S12).

The related information archive part 32 records by linking the operated medical image with the start time of the operation and the type of operation (S13).

The process of S11 to S13 is repeated (in case of N in S14) until the generation of the medical report is completed, and if the generation of the medical report is completed (in case of Y in S14), the image operation in generating the medical report is complete, then the image operation history is recorded in the related information archive part 32 as operation history ID 100 for example as shown in FIG. 5 (S15).

(Regarding an Input History Recording Process)

Next, the input history recording process in the present embodiment is described in detail using FIG. 6 to FIG. 9C.

A radiologist enters findings in a findings input column while using a medical image displayed in the viewer part 4 as a reference to generate a medical report. In the present embodiment, a process of recording the history of the findings input (hereinafter, sometimes referred to as "input history") is conducted.

Figure 6:
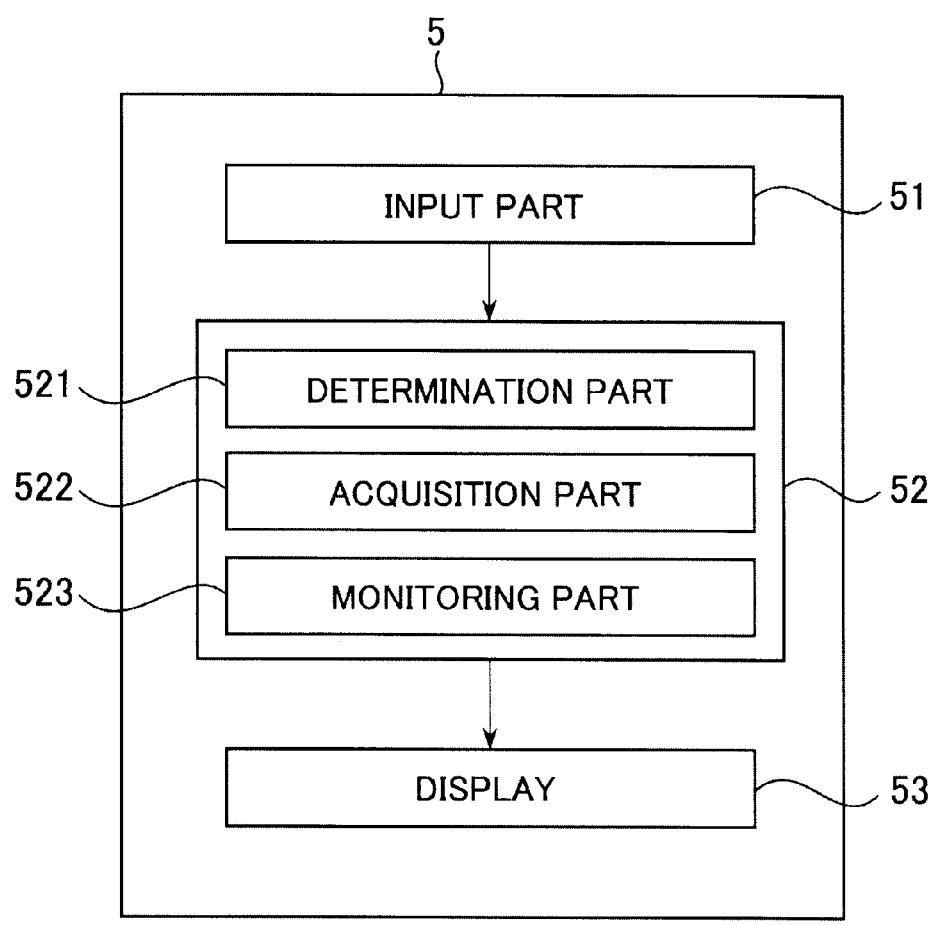
FIG. 6 is a diagram showing a configuration of a report part in an input history recording process according to the first embodiment.

As shown in FIG. 6, in the input history recording process, the CPU 52 functions as a determination part 521, an acquisition part 522, and a monitoring part 523.

The determination part 521 functions to determine the start of the findings input in a medical report and the end of the findings input.

Specifically, when the findings input column on the display 53 is selected using the input part 51, the findings input column is activated (a state in which the input of findings becomes possible). On the other hand, when the findings input using the input part 51 is completed, the findings input column is deactivated (a state in which the input of findings becomes impossible). The determination part 521 recognizes these activated or deactivated states based on input signals (a findings input column selection signal and a selection cancellation signal) from the input part 51 and determines the start of the findings input and the finish of the findings input.

The acquisition part 522 functions to acquire the time when the findings input column is activated (hereinafter, sometimes referred to as "input start time") and the time when the findings input column is deactivated (hereinafter, sometimes referred to as "input finish time").

Specifically, the corresponding time is acquired based on input signals (a findings input column selection signal and a selection cancellation signal) from the input part 51.

The monitoring part 523 functions to monitor the location, within the findings input column, of findings input using the input part 51. For example, for a case in which a finding has been written from the first letter to the $100^{th}$ letter in the findings input column (the former finding input), if a new finding is inserted from the $51^{st}$ letter to the $80^{th}$ letter on another occasion (the later finding input), the monitoring part 523 determines that the former findings input is from the first letter to the $50^{th}$ letter and the $80^{th}$ letter to the $130^{th}$ letter, and conducts a process of recording the determination result in the report archive part 36. Moreover, the monitoring part 523 determines that the later finding input is from the $51^{st}$ letter to the $81^{st}$ letter, and conducts a process of recording the determination result in the report archive part 36.

Furthermore, in the present embodiment, the report archive part 36 within the server part 3 functions to record by linking with the input start time of a finding and the input finish time as well as the location of the findings within the findings input column. That is, the report archive part 36 also functions as "an input history recording part." It should be noted that it is also possible to provide a recording part within the report part 5 and record input histories in the recording part.

Figure 7:
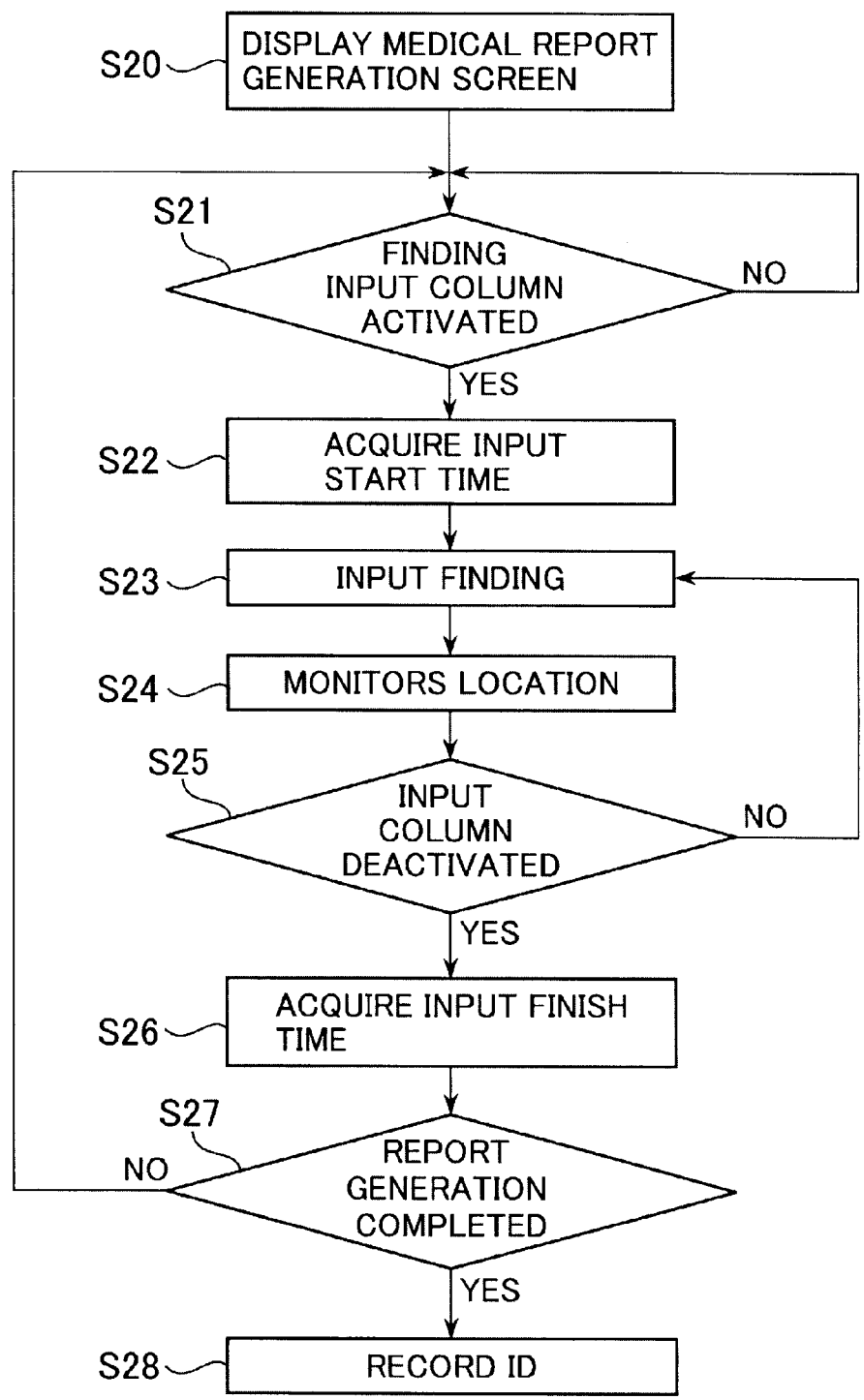
FIG. 7 is a flowchart of the input history recording process according to the first embodiment.

FIG. 7 is a flow chart of an input history recording process.

Based on instructions input from the input part 51, when a medical report generation screen is displayed on the display 53 (S20), the determination part 521 first determines whether the findings input column in the medical report generation screen is activated or not (S21).

If the findings input column is activated (in case of Y in S21), the acquisition part 522 acquires the input start time (S22).

In the findings input column that has been activated, the findings with respect to a medical image displayed in the viewer part 4 are input using the input part 51 (S23).

In a state in which the finding input is executed in S23, the monitoring part 523 monitors the location within the findings input column where findings have been input (S24).

When findings input is complete (in case of Y in S25), according to the instructions from the input part 51, the activated state of the findings input column is cancelled (deactivated). If findings input is not complete (in case of N in S25), by returning to S23, the subsequent findings input continues.

When the findings input column is deactivated, the acquisition part 522 acquires the input finish time (S26).

When the necessary finding input is complete with respect to the findings input column, the generation of the medical report is complete (S27).

The input start time and the input finish time of each finding as well as the location of the findings written in the medical report are recorded in the report archive part 36 (S28). Specifically, for example, as shown in FIG. 8, the information is recorded as input history ID 200 in the report archive part 36. In the input history ID 200 shown in FIG. 8, a state in which the finding inputs have been made in a findings input column three times ((a) to (c)) at different timings.

Herein, as in FIG. 8, a process of the monitoring part 523 is described using FIG. 9 for a case in which the entry of finding inputs are made in the findings input column a plurality of times at different timings.

Figure 9A:
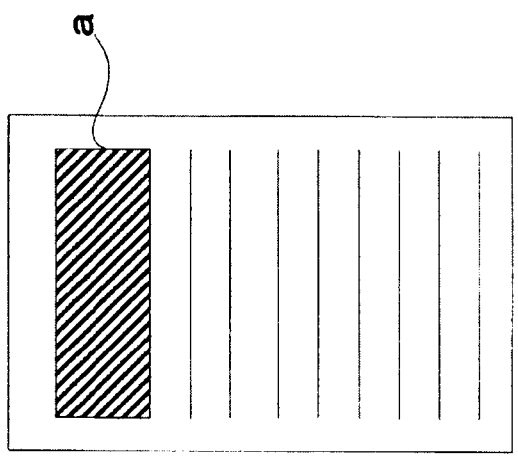
FIG. 9A is a supplementary diagram of the input history recording process according to the first embodiment.
Figure 9B:
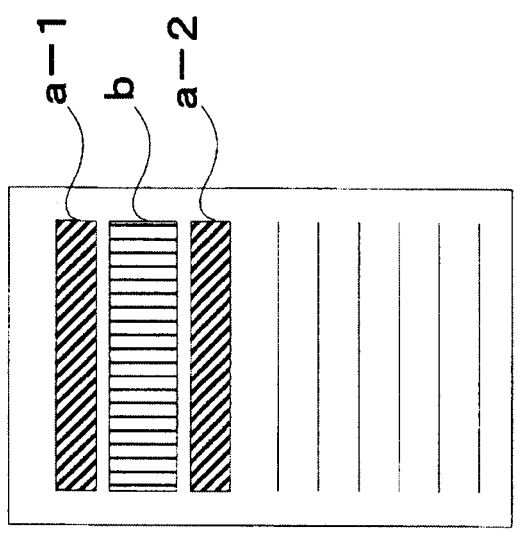
FIG. 9B is a supplementary diagram of the input history recording process according to the first embodiment.
Figure 9C:
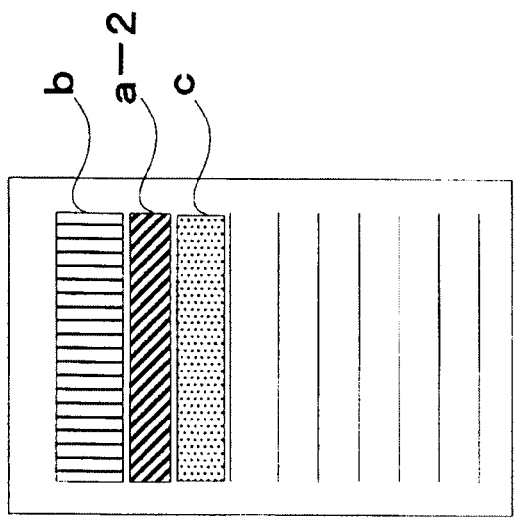
FIG. 9C is a supplementary diagram of the input history recording process according to the first embodiment.

For example, in a state in which a finding "a" (location of findings: first letter to a first letter of the $160^{th}$ letter) for which the input has finished at a timing in the findings input column has been written (ref. FIG. 9A), if a new finding "b" is inserted in the middle of the finding "a" at a different timing (location of findings: the $101^{st}$ letter to the $150^{th}$ letter), as shown in FIG. 9B, the finding "a" are divided into two, namely, findings "a-1" (location of findings: first letter to the $100^{th}$ letter) and findings "a-2" (location of findings: the $151^{st}$ letter to the $160^{th}$ letter). However, the monitoring part 523 monitors the divided findings "a-1" and "a-2" as findings for which the input was started at the same time and the input was ended at the same time (findings for which the input process was conducted at the same timing). Therefore, in the report archive part 36, a state ((a) and (b) in FIG. 8) in which the input start time as well as the input finish time of the findings "a" and the findings "b" remain separated, is recorded as is. Likewise, as in FIG. 9C, even when new findings "c2 (location of findings: the 161" letter to the $200^{th}$ letter) are added and the findings "a-1" are deleted, in the report archive part 36, a state ((a) to (c) in FIG. 8) in which the input start time as well as the input finish time for each of findings "a-2", findings "b", and findings "c" remain separated, is recorded as is. It should be noted that with regard to the location of letters in a medical report, if the finding "a-1" is deleted, the finding "a-2" becomes the $51^{st}$ letter to the $60^{th}$ letter, the finding "b" becomes the first to the $50^{th}$ letter, and finding "c" becomes the $61^{st}$ to $100^{th}$ letter, respectively.

The trigger for the acquisition part to acquire the start time and the finish time of findings input is not limited to the activation or deactivation of the findings input column. For example, it is also possible to acquire the input start time of one sentence as a finding input start time and acquire the input completion time of the sentence (the time when a period is input) as an input finish time.

(Regarding the Focus Image Extracting Process)

Next, with respect to medical reports in which the image operation history as well as the input operation history described above have been recorded, the process of a radiologist displaying focus images corresponding to the findings in the medical report is explained.

Figure 10:
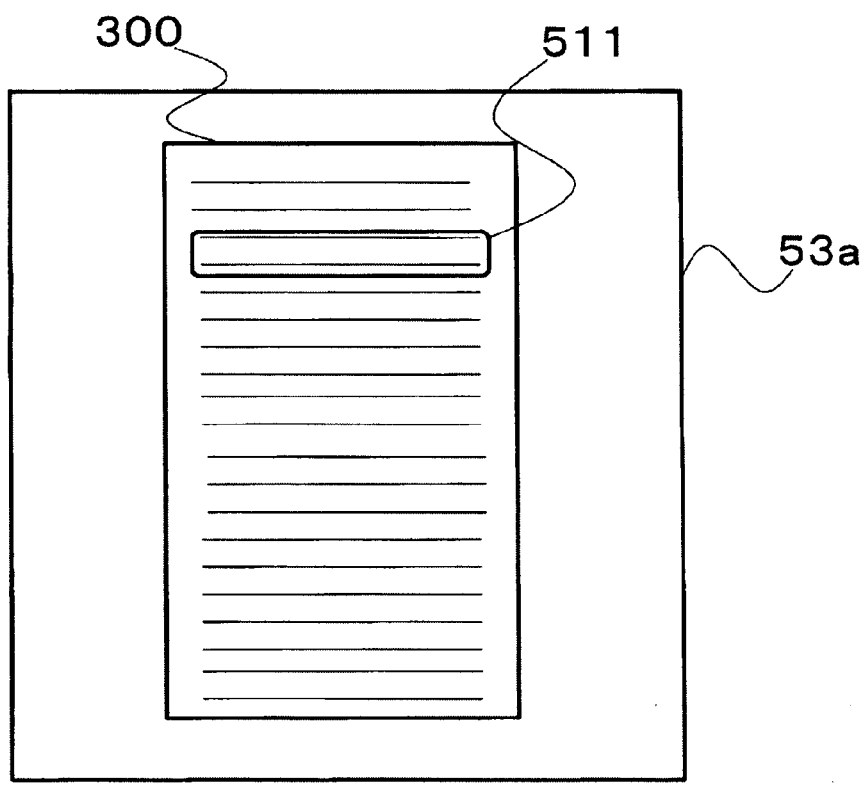
FIG. 10 is a diagram showing a selection part in a focus image extracting process according to the first embodiment.

As shown in FIG. 10, in the present embodiment, the selection part 511 is provided in the display screen 53a on the display 53. The selection part 511 is operated by using the input part 51 and functions to select at least a part of the findings written in a medical report 300 that is displayed in the display screen 53a on the display 53.

Figure 11:
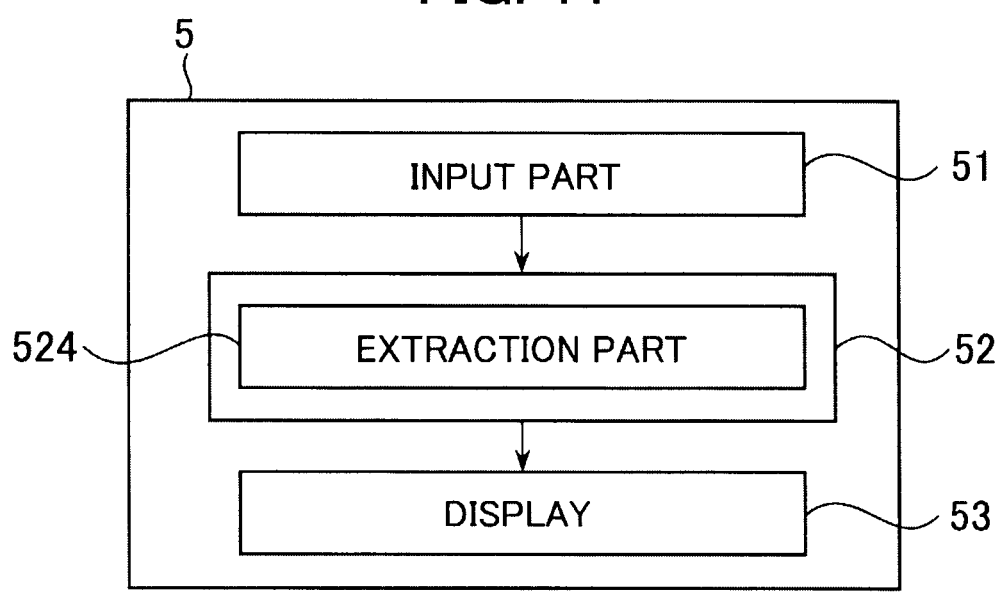
FIG. 11 is a diagram showing a report part in the focus image extracting process according to the first embodiment.

Furthermore, as shown in FIG. 11, the CPU 52 functions as an extraction part 524 in a focus image extracting process.

The extraction part 524 functions to extract a focus image corresponding to a finding that is selected by the selection part 511 based on the input history of the findings selected by the selection part 511 and the operation history conducted with respect to an image that was used as a reference when the finding was input. The details of extracting a focus image are described later.

Figure 12:
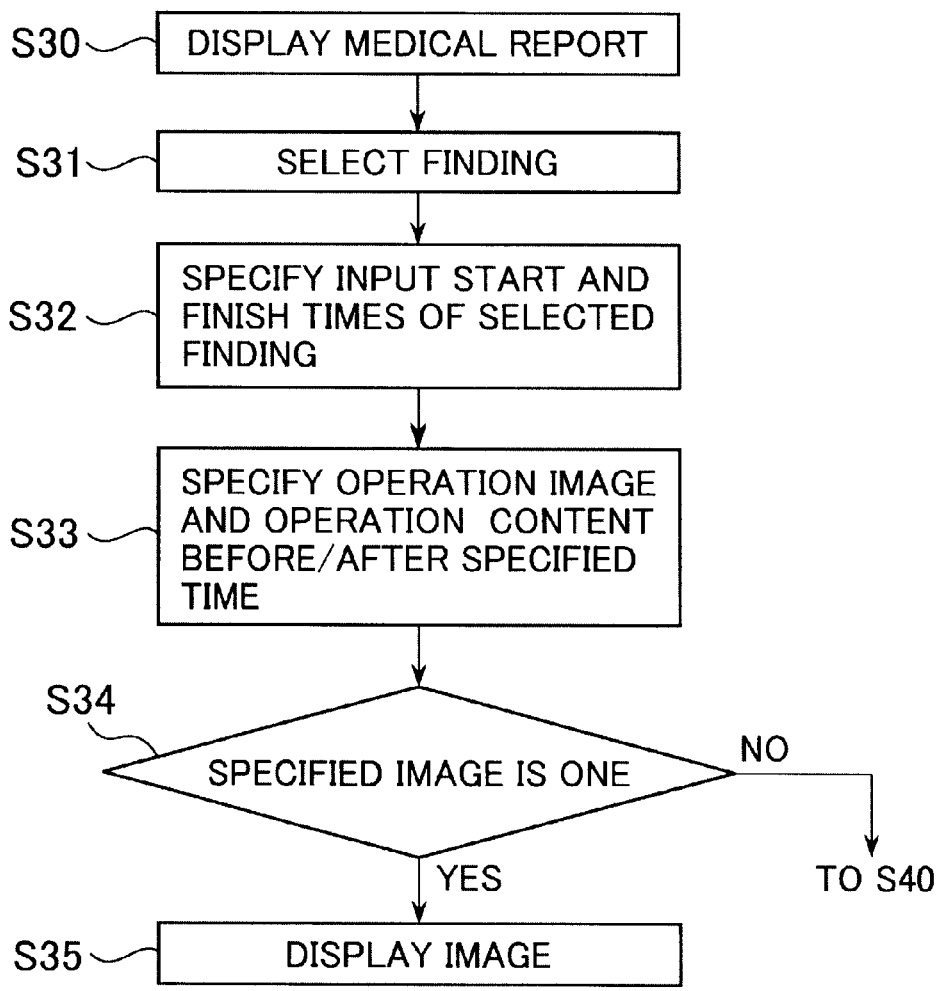
FIG. 12 is a flowchart of the focus image extracting process according to the first embodiment.
Figure 13:
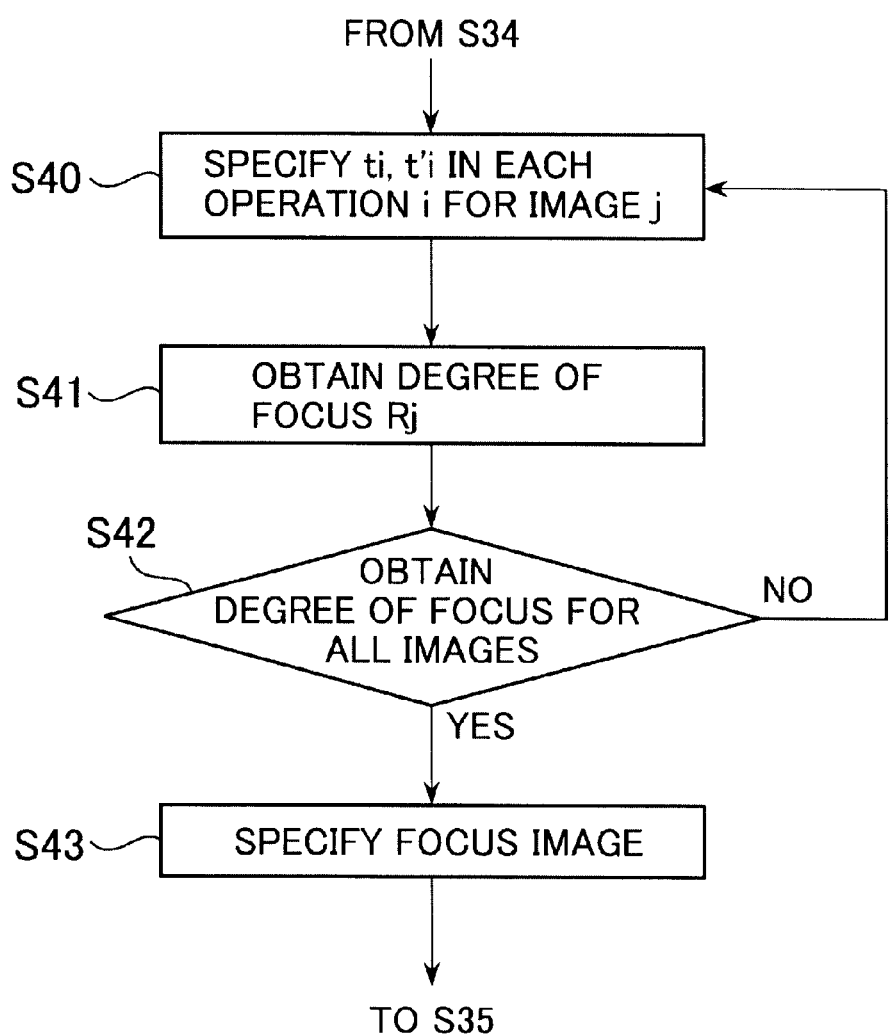
FIG. 13 is a flowchart of the focus image extracting process according to the first embodiment.

FIG. 12 and FIG. 13 are flow charts of a focus image extracting process.

First, when a radiologist inputs a patient ID, etc. from the input part 51, the medical report related to a previous examination corresponding to the patient ID is displayed on the display 53 (S30).

Herein, with regard to a finding in the medical report, if the radiologist wishes to see an image that has been focused in the event of writing the finding, the radiologist operates the input part 51 and selects a desired finding by moving the selection part 511 that is shown as a marker (S31. ref. FIG. 10).

When a finding is selected by the selection part 511, the extraction part 524 reads out, from the report archive part 36, the input history ID 200 related to the input history corresponding to the medical report, and conducts a process of specifying the input start time as well as the input finish time of the finding selected by the selection part 511 (S32). For example, when the finding from the $100^{th}$ letter to the $150^{th}$ letter in a medical report is selected by the selection part 511, the extraction part 524 specifies the input start time as well as the input finish time of the finding from the input history ID 200.

Next, the extraction part 524 reads out an operation history ID from the related information archive part 32 and conducts a process of specifying an image that has been operated before/after the time specified in S32 as well as the content of a conducted operation (S33).

Herein, if the specified image in S33 is one sheet (in case of Y in S34), the image is considered to be an image that has been displayed when the finding selected by the selection part 511 was input.

Therefore, the extraction part 524 instructs the CPU 42 to cause the display 43 to display the image as a focus image. Based on the instructions, the CPU 42 reads out the image from the image archive part 33 and controls so as to cause the display 43 to display the image (S35). That is, in the present embodiment, the CPU 42 functions as a "display controller."

On the other hand, if there are a plurality of sheets of images specified in S33 (in case of N in S34), the extraction part 524 conducts a process of specifying an image (focus image) related to the finding selected by the selection part 511 among images specified in S33 (S40 to S43).

Herein, the process of specifying a focus image is described in detail. In the following description, the time when the input of findings selected by the selection part 511 has started is a start time $t_S$, the time when the input of findings selected by the selection part 511 has ended is a finish time $t_E$, a prescribed period set prior to the start time $t_S$ is T, and a prescribed period set after the finish time $t_E$ is T'. Furthermore, in an operation "i" conducted with respect to an image "j", the time when operation was conducted within the period T is $t_i$ and the time for some operation within the period T' is $t'_i$. It should be noted that an operation that has not actually been conducted is $t_i = t_S - T$, $t'_i = t_E + T'$.

The period T and the period T' are values that have been preliminarily recorded in the server part 3, etc., but they may also be determined by inputting an arbitrary value by the input part 51, etc. in the event of an extracting process.

Furthermore, in the present embodiment, the report archive part 36 has table data in which various types of operations with respect to a medical image are weighed, for example, as shown in Table 1. Here, "Weight Wi" is a value that is used to specify the importance of the image on which the operation is performed. In the present embodiment, if the value "i" is greater, the operation is regarded as more important.

TABLE 1

| No. | Operation type | Weight Wi |
|---|---|---|
| 1 | Opening an image | W1 |
| 2 | Closing an image | W2 |
| 3 | Enlargement/Reduction | W3 |
| 4 | Gradation change | W4 |
| 5 | Coordinate shift | W5 |
| 6 | Annotation | W6 |

Herein, the following equation (1) represents the degree of focus $R_j$ which is a value indicating the linkage degree of an image "j" with findings selected by the selection part 511.

[Equation 1]

$$R_j = \sum_i W_i \times \{T - (t_S - t_i)\} + \sum_i W_i \times \{T' - (t'_i - t_E)\} \quad (1)$$

As is clear from the equation (1), for the extraction part 524, images subjected to important operations (greater weighed operations) are recognized as images with greater possibilities of being related to the finding selected by the selection part 511.

Furthermore, for the extraction part 524, with regard to images subjected to operations in a period of period T or period T', if the time of the operation is closer to a start time $t_S$ or a finish time $t_E$, the image is recognized as possibly being related to the findings selected by the selection part 511.

As a specific process for specifying a focus image, first, the extraction part 524 specifies $t_i$ and $t'_i$ in each operation "i" that was conducted with respect to the image "j" (S40).

Next, the extraction part 524 uses the equation (1) and conducts a process of obtaining the degree of focus $R_j$ with respect to the image "j" (S41). Furthermore, the extraction part 524 conducts a process of obtaining the degree of focus $R_j$ with respect to all images specified in S34 (in case of N in S42).

When the process of obtaining the degree of focus with respect to all the images specified in S34 is complete (in case of Y in S42), images with greater values of degree of focus are specified as images (focus images) having an association with the findings selected by the selection part 511 (S43). In this case, for example, it is possible to specify an image with the greatest value in the degree of focus as a focus image. Otherwise, it is also possible to specify all images with a higher degree of focus than a threshold value as focus images.

Furthermore, images indicating values at higher levels among a plurality of obtained degrees of focus (for example, images with a degree of focus in the top 10% of the degree of focus) may also be specified as focus images.

Herein, the extraction part 524 instructs the CPU 42 to cause the display 43 to display the images specified in S43 as focus images. The CPU 42 reads out the images from the image archive part 33 based on the instructions and controls so as to cause the display 43 to display the images (S35).

It should be noted that in the present embodiment, the weight of each operation and the time when these operations were conducted are used for an extraction process, but this process is not limited to this.

For example, by only focusing on the time when an operation was conducted, an image subjected to an operation at a time close to the start time $t_S$ or the finish time $t_E$ may be specified as a focus image. In this case, the image subjected to an operation at the time closest to the start time $t_S$ or the finish time $t_E$ may be specified as a focus image. Otherwise, it is also possible to specify all images subjected to operations at a time closer to the start time $t_S$ or the finish time $t_E$ rather than to a threshold value. Furthermore, among images subjected to operations, the top images close to the start time $t_S$ or the finish time $t_E$ (for example, images in the top 10% of the time close to the start time $t_S$ or the finish time $t_E$) may also be specified as focus images.

Otherwise, it is also possible to specify, as focus images, images subjected to a highly weighed operation in a certain period T. In this case, an image subjected to the highest weighed operation in a certain period T may be specified as a focus image. Otherwise, it is also possible to specify, as a focus image, all images subjected to operations weighing higher than a threshold value in a certain period T. Furthermore, among images subjected to operations in a certain period T, it is also possible to specify, as focus images, the top weighing images (for example, high weighing images in the top 10%).

Moreover, focus images may be extracted using the frequency of each operation instead of weighing. Or, it is also possible to extract focus images using the number of times when operations were conducted to a certain image.

Furthermore, in the present embodiment, the image operation history recording process and the input history recording process are conducted in real time. Therefore, specifying focus images is possible even in the midst of generating a medical report.

Moreover, in the input history, the time linked to a location in a medical report of findings input at the time of generating the medical report need to be simply at least one of an input start time and a finish time of the findings.

As described thus far, in the present embodiment, the configuration is capable of easily displaying focus images with respect to a finding of a medical report based on the input history and the operation history. Therefore, when a radiologist, etc. uses, as a reference, a medical report of a previous examination, because it becomes possible to easily acquire a focus image corresponding to the findings written in the medical report, the interpreting efficiency is improved.

Embodiment 2

Figure 14:
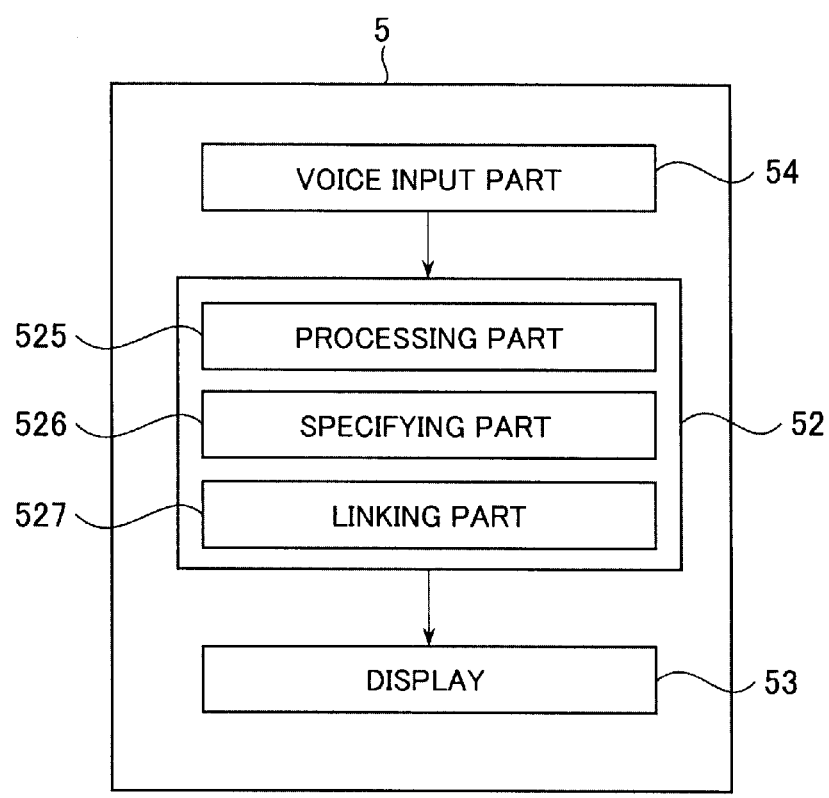
FIG. 14 is a diagram showing a configuration of a report part in an input history recording process according to a second embodiment.
Figure 15:
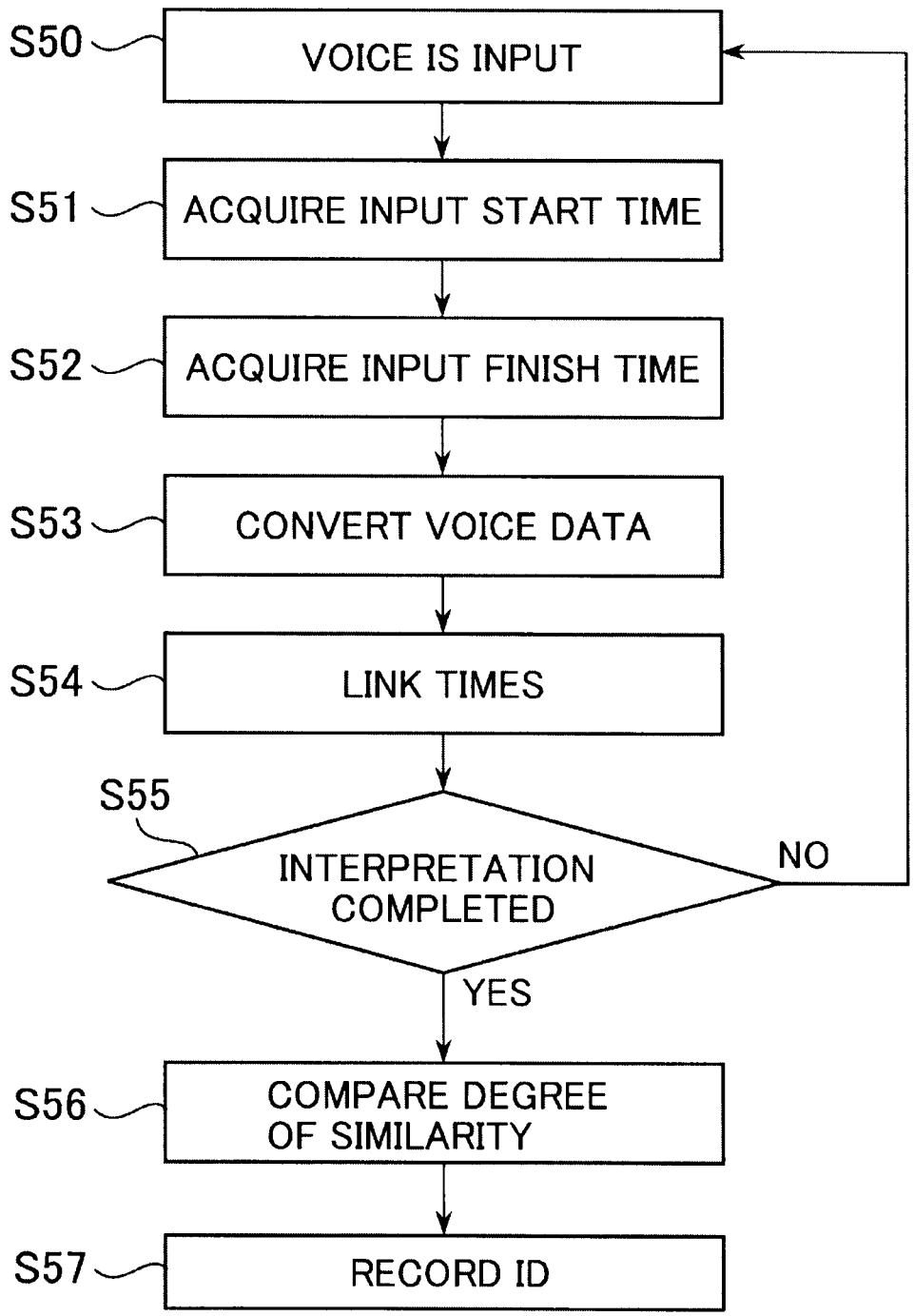
FIG. 15 is a flowchart of the input history recording process according to the second embodiment.

Embodiment 2 is described using FIG. 14 and FIG. 15. The difference between Embodiment 1 and Embodiment 2 is the input history recording process. Therefore, the details are omitted for the description regarding other configurations or processes. It should be noted that because "voice" and "voice data" have one-to-one correspondence, sometimes they are considered to be the same in the present embodiment.

(Regarding an Input History Recording Process)

When generating a medical report, sometimes there is an intervention by a dictator (human). That is, a radiologist uses a voice input means such as a microphone and records the verbally stated contents in the report part 5, etc. while using medical images displayed in the viewer part 4 as references. Thereafter, the dictator listens to the record and inputs the findings in a findings input column based on the verbally stated content. In this case, it is possible that a slight difference could be generated between the actual content stated verbally by the radiologist and the findings input by the dictator. For example, sometimes those judged as clearly irrelevant (for example, interjections) to the findings among the verbally stated contents are omitted in the input by the dictator. In the present embodiment, an input history recording process for such a case is described.

As shown in FIG. 14, in the present embodiment, a voice input part 54 is provided in the report part 5. The voice input part 54 is a means for inputting verbally stated content in a form of voice when a radiologist, etc. conducts the interpretation. The input voice is converted to voice data and sent to the CPU 52. It should be noted that as long as the voice input part 54 is connected so as to be communicable via the LAN 6, said voice data does not have to be provided in the report part 5. Furthermore, in addition to the voice input part 54, the report part 5 may also have an input part 51 as in Embodiment 1.

Moreover, as shown in FIG. 14, in the input history recording process in the present embodiment, the CPU 52 functions as a processing part 525, a specifying part 526 and a linking part 527.

The processing part 525 functions to analyze voice data based on the voice input from the voice input part 54 and converts the voice data to text data. Furthermore, the processing part 525 functions to conduct a process of linking the text data with an input start time and an input finish time of the voice data as its source. Specifically, along with inputting a voice, the processing part 525 acquires the input start time s1 of the voice. Furthermore, when the voice input is complete, the processing part 525 acquires an input finish time e1. Moreover, the processing part 525 analyses voice data "a" based on the voice input, and converts the voice data "a" to text data "A". The processing part 525 also links the text data "A" with an input start time s1 and an input finish time e1. The processing part 525 repeats this process while a voice is being input (for example, an input start time s2 and an input finish time e2 are linked with text data "B", an input start time s3 and an input finish time e3 are linked with text data "C", . . . ). The process results obtained by the processing part 525 are recorded in the recording part (not illustrated) within the report part 5.

The input start time and the input finish time of voice data are obtained, for example, by specifying from an input of voice data to a breakpoint of the voice data (a period in the text) by in the processing part 525. It should be noted that it is also possible to provide a switch for turning on/off the voice input part 54 and make note of the point when the processing part 525 detects the switch as having been turned on as an input start time and the point when the switch as having been turned off is detected as the finish time.

The specifying part 526 functions to compare the text data converted in the processing part 525 and findings in a medical report generated based on a voice input from the voice input part 54, and specify similar text data and findings. Specifically, the degree of similarity between the findings in a medical report generated by the dictator and text data are compared and those with high degree of similarities are specified as the same content. For example, with regard to findings "A'" in a medical report, the specifying part 526 compares the degree of similarity with text data "A" to "C", and specifies the text data "A" with the highest degree of similarity as the same content.

It should be noted that even if the order of the text data and the order of the findings in a medical report are different (for example, when a dictator shuffles the order of voice data, and generate a medical report), it is possible for the specifying part 526 to specify findings and text data in the same content by comparing the degree of similarity between the findings in a medical report and text data.

The linking part 527 functions to record, in the report archive part 36, an input start time and a finish time linked with the text data specified in the specifying part 526 as input history by also linking with the findings specified in the specifying part 526. Specifically, the linking part 527 links, also with the findings A' specified in the specifying part 526, the input time s1 and the finish time e1 linked with the text data "A" specified by the specifying part 526. Once linking with respect to all findings is complete, the results are recorded in the report archive part 36 as an input history ID. In the present embodiment, "at the time of generating a medical report" refers to the timing starting from a voice input by the voice input part 54 until the input history is recorded in the report archive part 36 by the linking part 527.

FIG. 15 is a flow chart of an input history recording process in the present embodiment.

When a voice is input from the voice input part 54 (S50), the processing part 525 acquires the input start time of the voice (S51).

Furthermore, once a single voice input is complete, the processing part 525 acquires the input finish time (S52). Moreover, the processing part 525 analyses single voice data based on the voice that has been input in S50, and converts the voice data to single text data (S53).

The processing part 525 links the single text data converted in S53 with the input start time acquired in S51 and the input finish time acquired in S52 (S54). The processing part 525 repeats this process while voice data is being input (in case of N in S55).

For case when the input of the voice data is completed (in case of Y in S55), the specifying part 526 compares the degree of similarity between the findings in the medical report generated by the dictator based on the voice data input in S50 and the text data converted in S53, and specifies those with a high degree of similarity as the same content (S56).

Moreover, the linking part 527 causes the report archive part 36 to record the input start time and the input finish time linked with the text data specified in S56 by also linking with the findings specified in S56 as an input history ID (S57).

It should be noted that the time to be linked with the text data by the processing part 525 may be at least one of an input start time and a finish time of voice data which is a base of the text data.

As in the present embodiment, even for cases of inputting findings using a voice, the configuration is capable of easily displaying focus images with respect to a certain finding in a medical report based on the input history and the operation history. Therefore, if a radiologist, etc. uses medical reports from previous examinations as a reference, it becomes possible to easily acquire a focus image corresponding to the finding written in the medical report, thus, improving the interpreting efficiency.

While certain embodiments have been described, these embodiments have been presented by way of example only, and are not intended to limit the scope of the inventions. Indeed, the novel systems described herein may be embodied in a variety of their forms; furthermore, various omissions, substitutions and changes in the form of the systems described herein may be made without departing from the spirit of the inventions. The accompanying claims and their equivalents are intended to cover such forms or modifications as would fall within the scope and spirit of the inventions.

What is claimed is:

1. A report generation support system comprising:
   a medical image generator configured to generate a medical report together with entry of an operation on a medical image among a plurality of medical images;
   an input history recording part configured to record, as an input history, findings input at a time of generating the medical report by linking with at least one of an input start time and a finish time of the findings;
   an operation history recording part configured to record, as an operation history, a type of operation conducted with respect to the medical image operated at the time of generating said medical report and a time when the operation is conducted by linking with the operated image;
   a selection part configured to select, based on instructions input from an input part, at least a part of the findings in the medical report;
   an extraction part configured to extract a focus image in the findings selected by said selection part from among the plurality of medical images, based on at least one of the input start time and the finish time of findings corresponding to a location selected by said selection part and contents of said operation history of the corresponding time; and
   a display controller configured to cause a display to display said focus image.

2. The report generation support system according to claim 1, wherein said input history recording part is configured to record, as the input history, the location in the medical report of the findings that is input at the time of generating said medical report by linking at least one of the input start time and the finish time of the findings.

3. The report generation support system according to claim 1, further comprising a voice input part configured to receive input of a voice of said findings at the time of generating said medical report, wherein
   said input history recording part is configured to record, with respect to the findings of the medical report generated based on said voice as an input history by linking with at least one of an input start time and a finish time linked to the voice similar to the findings.

4. The report generation support system according to claim 1, wherein the contents of said operation history include a weight with respect to each type of operation conducted at a time corresponding to at least one of said input start time and said input finish time, and the time when each of the operations was conducted.

5. The report generation support system according to claim 1, wherein the contents of said operation history include a weight with respect to each type of operation conducted at a time corresponding to at least one of said input start time and said input finish time, or the time when each of the operations was conducted.

6. The report generation support system according to claim 1, wherein said extraction part is configured to calculate a degree of focus indicating a degree of linkage with the findings selected by said selecting part based on said operation history, and extract said focus image based on the degree of focus.

\* \* \* \* \*